United States Patent
Teoh

[19]

[11] Patent Number: 6,139,564
[45] Date of Patent: Oct. 31, 2000

[54] MINIMALLY OCCLUSIVE FLOW DISRUPTOR STENT FOR BRIDGING ANEURYSM NECKS

[75] Inventor: Clifford Teoh, Daly City, Calif.

[73] Assignee: Target Therapeutics Inc., Fremont, Calif.

[21] Appl. No.: 09/098,124

[22] Filed: Jun. 16, 1998

[51] Int. Cl.[7] .................................................. A61B 17/04
[52] U.S. Cl. .......................................................... 606/213
[58] Field of Search ................................. 606/139, 151, 606/213, 191; 623/11, 12

[56] References Cited

U.S. PATENT DOCUMENTS

| | | | |
|---|---|---|---|
| 4,739,768 | 4/1988 | Engelson | 128/658 |
| 4,820,298 | 4/1989 | Leveen et al. | 606/191 |
| 4,994,069 | 2/1991 | Ritchart et al. | |
| 5,122,136 | 6/1992 | Guglielmi et al. | 606/32 |
| 5,135,494 | 8/1992 | Engelson et al. | 604/99 |
| 5,250,071 | 10/1993 | Palermo | 606/198 |
| 5,258,042 | 11/1993 | Metha | 623/66 |
| 5,261,916 | 11/1993 | Engelson | 606/108 |
| 5,354,295 | 10/1994 | Guglielmi et al. | 606/32 |
| 5,593,422 | 1/1997 | Van De Moer et al. | 606/213 |
| 5,609,628 | 3/1997 | Keranen | 623/1 |
| 5,620,461 | 4/1997 | Van De Moer et al. | 606/213 |
| 5,879,366 | 3/1999 | Shaw et al. | 606/213 |
| B1 4,739,768 | 11/1994 | Engelson | 128/658 |
| B2 4,739,768 | 10/1995 | Engelson | 128/658 |

FOREIGN PATENT DOCUMENTS

| | | |
|---|---|---|
| 0 664 104 A2 A3 | 7/1995 | European Pat. Off. . |
| WO 97/48351 | 12/1997 | WIPO . |

*Primary Examiner*—Gary Jackson
*Attorney, Agent, or Firm*—Morrison & Foerster LLP

[57] ABSTRACT

This is a device for bridging the neck of a wide-necked or narrow-necked aneurysm in the vasculature. In general, it is a device used to stabilize aneurysms found in the vasculature by at least partially closing the opening to that aneurysm with consequent limiting of the amount of blood flowing into and out of the chamber. The device is generally made of a metallic or polymeric sheet and is of a shape which may be deployed using a catheter. The device typically has three major components: the central closure area, the centrifugal stabilizers, and the axial stabilizers. The device is intended to be a permanent implant and may be used with or without occlusive devices and materials placed inside the aneurysm volume.

11 Claims, 5 Drawing Sheets

1

MINIMALLY OCCLUSIVE FLOW DISRUPTOR STENT FOR BRIDGING ANEURYSM NECKS

FIELD OF THE INVENTION

This invention is a device for bridging the neck of a wide-necked or narrow-necked aneurysm in the vasculature. In general, it is a device used to stabilize aneurysms found in the vasculature by at least partially closing the opening to that aneurysm with consequent limiting of the amount of blood flowing into and out of the chamber. The device is generally made of a metallic or polymeric sheet and is of a shape which may be deployed using a catheter. The device typically has three major components or regions: the central area, the centrifugal stabilizers, and the axial stabilizers. The device is intended to be a permanent implant and may be used with or without occlusive devices and materials placed inside the aneurysm volume. It may be delivered by introduction through or on a catheter or via a delivery wire.

BACKGROUND OF THE INVENTION

Various implantable medical devices have been developed for treating ailments in the vascular system. Vaso-occlusive devices have been used extensively in closing regions of the vascular system. These devices are especially useful in treating aneurysms. Vascular aneurysms are formed as a result of a weakening in the wall of an artery and subsequent ballooning of the artery wall. Aneurysms are often a site of internal bleeding and, catastrophically, the site of strokes. A variety of different embolic agents are known to be suitable for treatment of such aneurysms. These treatments are commonly known as "artificial vaso-occlusion."

One such class of embolic agents includes injectable fluids or suspensions, such as microfibrillar collagen, various polymeric beads, and polyvinyl alcohol foam. These polymeric agents may additionally be crosslinked, sometimes in vivo to extend the persistence of the agent at the vascular site. These agents may be introduced into the vasculature through a catheter. After such introduction, materials there form a solid space-filling mass. Although some such agents provide for excellent short-term occlusion, many are thought to allow vessel recanalization due to absorption of polymer into the blood. Another procedure in which a partially hydrolyzed polyvinyl acetate (PVA) is dissolved in ethanol solvent and injected into a desired vascular site is found in Park et al. (U.S. patent application Ser. No. 08/734,442, filed Oct. 17, 1996, for "LIQUID EMBOLIC AGENTS").

Other materials, such as hog hair and suspensions of metal particles have also been suggested and used by those wishing to form occlusions.

Other materials, including polymeric resins, typically cyanoacrylates, are also employed as injectable vaso-occlusive materials. These resins are typically mixed with a radio-opaque contrast material or made radio-opaque by the addition of a tantalum powder. These materials are difficult to use in that the placement of the mixture in the body may be a problem. These materials cross-link within the human body. Inadvertent embolisms in normal vasculature, due to the inability of controlling the destination of the precursor resinous materials, is not uncommon. The material is also difficult or even impossible to retrieve once it has been placed into the vasculature.

Over the past few years, advancements in the artificial occlusion of vessels and aneurysms has occurred mostly due to the improvements in delivery and implantation of metal coils as vaso-occlusive devices. Implantable metal coils that are useful in artificial occlusion devices in vasculature lumens or aneurysms are herein referred to as "vaso-occlusive coils."

Vaso-occlusive coils are generally constructed of wire, usually made of a metal or metal alloy, that is first wound into a helix. Many such devices are introduced to the selected target site through a catheter in a stretched linear form. The vaso-occlusive device may assume an irregular shape upon discharge of the device from the distal end of the catheter. A variety of vaso-occlusive coils and braids are known. For instance, U.S. Pat. No. 4,994,069, to Ritchart et al., shows a flexible, preferably coiled, wire for use in small vessel vaso-occlusion. These coils are described as being between 0.010 and 0.030 inches in diameter. The wire used to make up the coils may be, for instance, 0.002 to 0.006 inches in diameter. Tungsten, platinum, and gold threads or wires are said to be preferred. These devices may be used to fill aneurysms.

It is common that these vaso-occlusive devices be delivered through microcatheters such as the type shown in U.S. Pat. No. 4,739,768, to Engelson. These microcatheters track a guidewire to a point just proximal or within the desired occlusion site. The vaso-occlusive coils are then advanced through the microcatheter, once the guidewire is removed, and out the distal end hole so to at least partially fill the selected site and create occlusion within the aneurysm.

In addition to the various types of space-filling mechanisms and geometries of vaso-occlusive coils, other particularize features of coil designs, such as mechanisms for delivering vaso-occlusive coils through delivery catheters and implanting them in desired occlusion sites, have also been described. Examples of such vaso-occlusive devices based upon their delivery mechanisms include pushable coils (see Ritchart et al., discussed above), mechanically detachable vaso-occlusive devices (see U.S. Pat. No. 5,261,916 to Engelson or U.S. Pat. No. 5,250,071 to Palermo), or electrolytically detachable vaso-occlusive devices (see U.S. Pat. Nos. 5,122,136 and 5,354,295 to Guglielmi et al.).

Each of the devices described above may be used in the treatment, by occlusion, of aneurysms. As noted above, aneurysms present particularly acute medical risks due to the dangers of potential rupture of the thin wall inherent in such a vascular anomaly. Occlusion of aneurysms by the use of vaso-occlusive coils without occluding the adjacent artery is a special challenge.

As noted above, the use of vaso-occlusive coils in treating aneurysms is widespread. These vaso-occlusive devices are placed in an aneurysm by the use of a microcatheter. The distal end of the microcatheter is advanced into the mouth of the aneurysm. The vaso-occlusive coil is then advanced through and out of that microcatheter. After, or perhaps during, delivery of such a coil into the aneurysm, there is a specific risk that a portion of the coil might migrate out of the aneurysm entrance zone and into the feeding vessel. The presence of such a coil in that feeding vessel may cause the undesirable response of causing an occlusion there. Also, there is a quantifiable risk that the blood flow in the vessel and the aneurysm may induce movement of the coil farther out of the aneurysm, resulting in a more thoroughly developed embolus in the patent vessel.

Furthermore, one type of aneurysm, commonly known as a "wide-neck aneurysm" is known to present particular difficulty in the placement and retention of vaso-occlusive coils. Wide-neck aneurysms are herein referred to as aneurysms of vessel walls having a neck or a "entrance zone" from the adjacent vessel, which entrance zone has a diameter of either (1) at least 80% of the largest diameter of the aneurysm; or (2) is clinically observed to be too wide effectively to retain vaso-occlusive coils that are deployed using the techniques discussed herein.

Furthermore, vaso-occlusive coils lacking substantial secondary shape strength may be difficult to maintain the position within an aneurysm no matter how skillfully they are placed.

There are a few disclosed devices for maintaining the presence of vaso-occlusive coils within an aneurysm. One such device is shown in U.S. Ser. No. 08/690,183, filed Jul. 26, 1996 for "ANEURYSM CLOSURE DEVICE ASSEMBLY" (Attorney Docket No. 29025-20162.00). That patent describes a number of devices which are to be placed within the lumen of a feed vessel exterior to the aneurysm. It may be used to retain coils within the aneurysm cavity. One highly desired way of using the device is this: the retainer device is released into the vessel exterior to the aneurysm. The device is held in place via the presence of radial pressure on the vessel wall. After the device is released and set in an appropriate place, a microcatheter is inserted into the lumen so that the distal end of the catheter is inserted into the aneurysm cavity. One or more vaso-occlusive devices is then introduced into the aneurysm cavity. The retainer device maintains the presence of the vaso-occlusive devices within the aneurysm whether it is a large-mouth aneurysm or not.

Other stents or grafts which may be used to seal the mouth of an aneurysm are shown, e.g., in U.S. Pat. No. 4,820,298, to Leveen et al.; U.S. Pat. No. 5,258,042 to Metha; and others. None of these devices are of the same configuration as that described herein.

SUMMARY OF THE INVENTION

This invention includes an implantable medical device useful for at least partially closing the opening to an aneurysm. It may further be used for retaining other occlusion devices within an aneurysm. The invention also relates to methods for introducing and installing the medical device at the selected site. In particular, the invention involves an implantable stent having a central closure area, opposing axially positioned struts extending from the closure area, and circumferential struts extending generally orthogonal to the axial struts. The device is desirably constructed from a metallic or polymeric sheet material and may be delivered using an intravascular catheter.

DESCRIPTION OF THE INVENTION

This invention involves the device and procedure for at least partially closing the mouth of an aneurysm, typically a small-necked aneurysm, and a method of placing that device in the vasculature. These closure devices may be used to maintain the presence of vaso-occlusive devices such as coils in an aneurysm.

Figure 1:
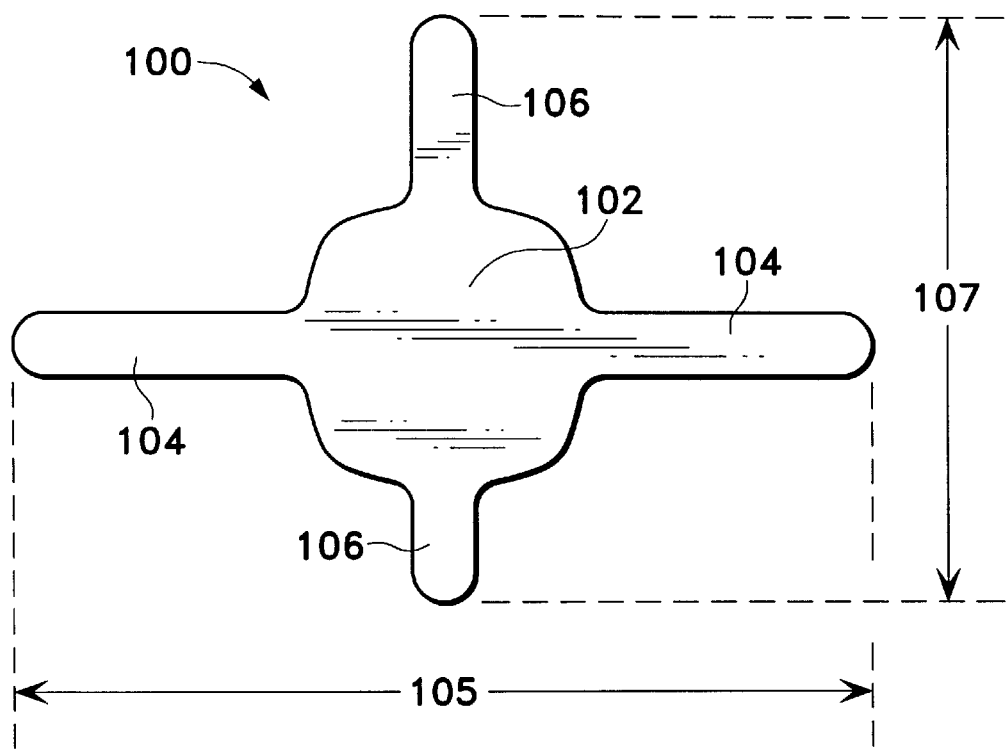
FIG. 1 shows a plan view of a generalized device made according to the invention and depicts the conventions used in describing the invention.

FIG. 1 is a plan view of an inventive device (100). It is made up, conceptually, of three major components. The first component is closure region (102). Closure region (102) is generally chosen by the physician introducing the device into the body to generally approximate the size of the aneurysm opening to be closed. It need not be that large in that the closure region may be sized so that only a portion of the aneurysm opening is covered. In this instance, the closure region merely operates to prevent passage of fresh blood into the aneurysm itself. To some extent, this partial closure will prevent the direct impingement of flowing blood on the weakened back wall of the aneurysm. Closure region (102) may be larger than the opening into the aneurysm but it need not be. Generally, it is most desirable to minimize the amount of material placed in these devices since that also minimizes the stiffness of the device when it is placed into the body through the vasculature.

Extending outwardly from the central or closure region (102) are a number of struts. The struts are usually paired so that they extend from the closure region (102) in generally opposite directions. In FIG. 1, axial struts (104) extend in generally opposite directions from closure region (102). Axial struts (104) are typically longer than their circumferential struts (106) since axial struts (104) are generally used to extend along the wall of an artery and parallel to the axis of the artery. Axial struts (104), it may be said, point in the direction of blood flow in the artery into which they are placed. Generally, the axial length (105) of the device is functionally simply long enough to prevent the device from rotating in the lumen of the blood vessel into which it is placed.

Similarly, the circumferential struts (106) extend outwardly from the closure region (102) and have a length (107) which desirably is greater than half of the circumference of the vessel into which it is placed so to maintain the closure region (102) reasonably firmly against the mouth of the aneurysm.

The device (100) typically may be made of metallic or polymeric materials. Typical metallic materials include stainless steel and the nickel-titanium alloys often used for their superelastic or shape-memory properties, the most common of which is known as nitinol. Thin polymeric sheets of reasonably pliable materials or composites of polymers and polymeric or metallic fibers. These devices desirably are constructed of materials which are not thrombogenic or may be coated with anti-thrombogenic materials. They may be coated with materials which are slippery and have a tendency, therefore, not to create occlusions. Inherently slippery polymers, such as many of the fluorocarbons and hydrophilic polymers, e.g., polyvinyl pyrrolidone, are members of these groups.

As noted above, these devices should be as thin as is reasonably possible so to make easy the insertion of the device. Depending upon the material used, stainless steel or superelastic alloys might be as thin as 0.25 mils (0.00025 inches) up to 15 mils, although typically no thicker than 7–12 mils.

Figure 2:
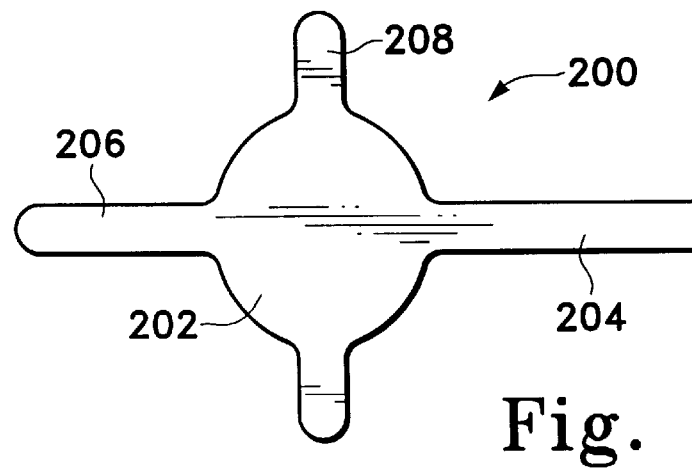
FIGS. 2 through 5 show plan views of various configurations of the invention.

FIGS. 2 through 5 show various configurations and aspect ratios of devices made according to this invention. FIG. 2, in particular, shows a device (200) in which the closure region (202) is circular and one axial strut (204) is longer than its opposing strut (206). Such a configuration may be desirable in instances where the aneurysm is on the exterior of a turn in an artery. In this variation, the circumferential struts (208) are narrow and of fairly short length.

Figure 3:
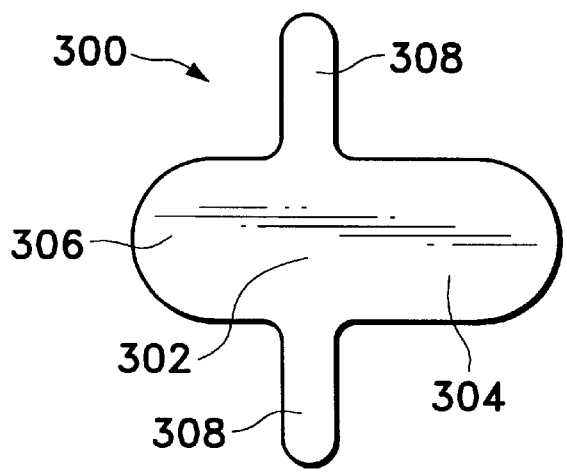

FIG. 3 shows another variation in which the closure region (300) in which the closure region (302) and the axial struts (304) and (306) each have identical diameters (as viewed vertically in FIG. 3). The circumferential struts (308) are also shown.

Figure 4:
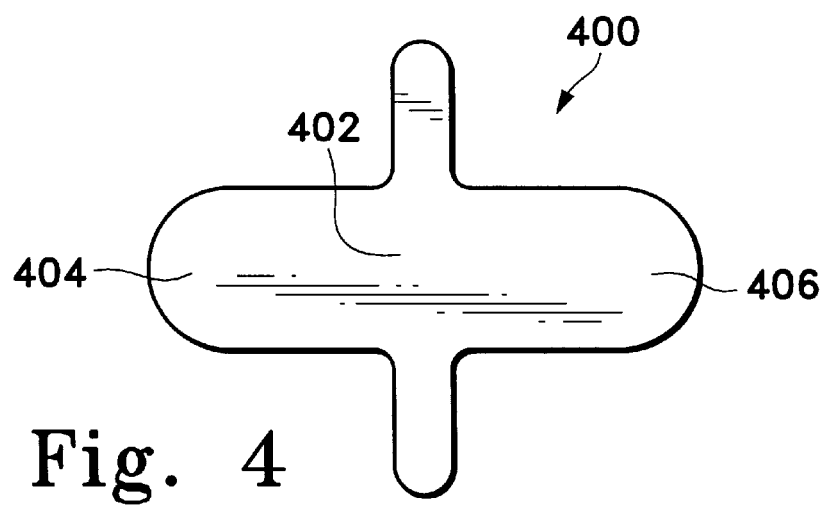

FIG. 4 shows a similar variation (400) in which the closure region (402) and the axial struts (404) and (406) have the same diameter. It should be noted that in FIG. 4 the upstream strut (404) is the same length as is the downstream strut (406). In contrast, the upstream strut (306) is shorter in FIG. 3 than is the downstream strut (304).

Figure 5:
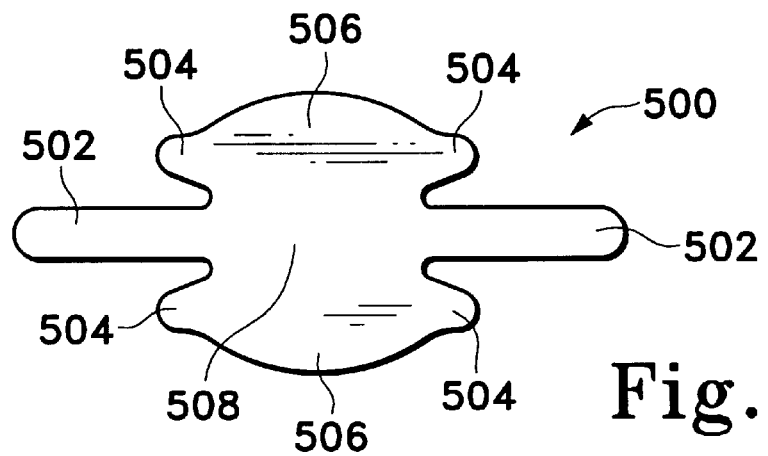

FIG. 5 shows still another variation of the invention (500). This variation may be used to cover a stent which has an oval mouth or is a so-called "wide-mouth" aneurysm. The device has the noted longitudinal struts (502) and supplemental longitudinal struts (504). The circumferential struts include, by area, the supplemental longitudinal struts (504). Each of these struts emanates from the closure region (508).

Figure 6A:
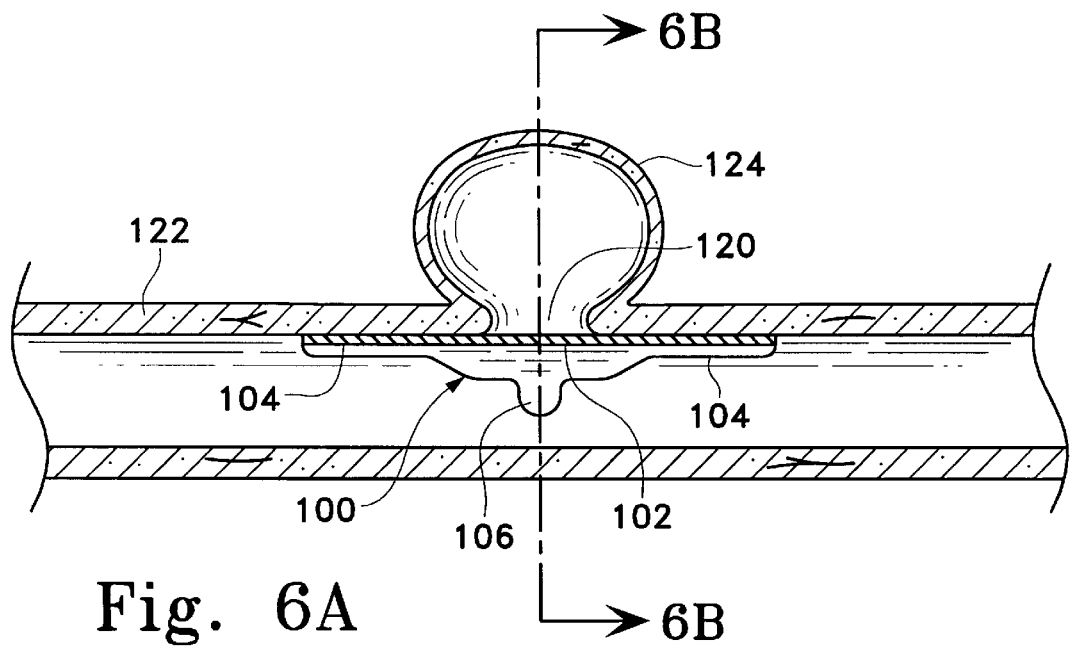
FIG. 6A shows a longitudinal view of an artery with an aneurysm showing placement of the device made according to the invention within the artery.
Figure 6B:
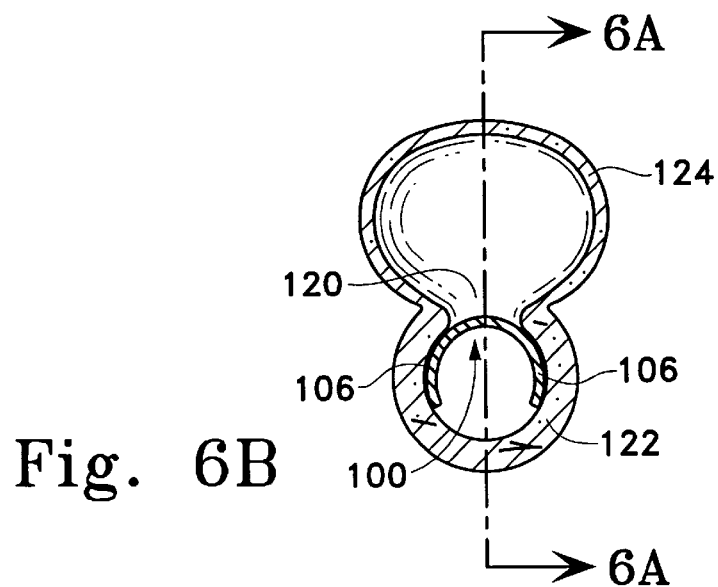
FIG. 6B shows a cross-sectional view of the view shown in FIG. 6A.

FIGS. 6A and 6B show the positioning of the inventive device (100) in an artery (122) over an aneurysm (124). The aneurysm has a mouth (120) as it enters the wall of artery (122). FIG. 6A is a cross-section side view of placement of the device (100) showing the desired positioning of the closure region (102) about the aneurysm opening (120). The FIG. 6A depiction also shows the positioning of the axial or longitudinal struts (104) along the axis of artery (122). The placement of circumferential struts (106) is also seen. It should be emphasized that FIGS. 6A and 6B show that the circumferential struts (106) desirably extend more than 180° around the circumference of the artery. This permits the device to stay in place and snugly against the mouth (120) of the aneurysm (124).

Figure 7A:
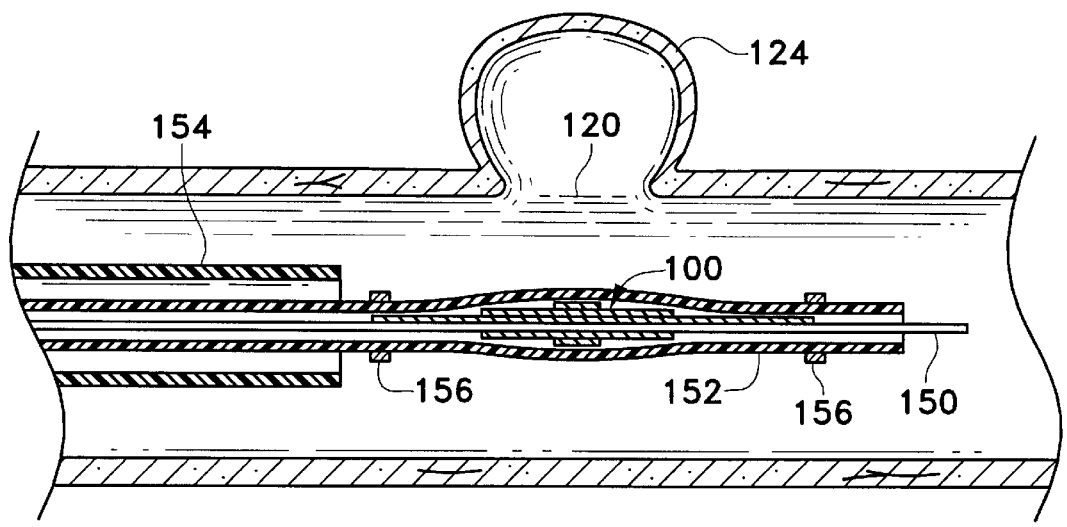
FIGS. 7A and 7B show in summary fashion the way in which the device may be deployed using an intravascular catheter.

FIG. 7A show a simplified procedure for placing the device (100) in the opening (120) of aneurysm (124). Desirably, device (100) is rolled tightly against a core wire (150) with a sheath (152) holding the rolled device (100) in place. The assembly is delivered to the mouth of aneurysm (124) using a catheter (154) of known design and size. It is desirable that the sheath (152) be marked using radio-opaque markers (156) of some type so that the device can be readily positioned about the mouth (120) of aneurysm (124). From the exterior of the body, core wire (150) is held in place while sheath (152) is pulled proximally to expose the inventive device and allow it to unroll.

Figure 7B:
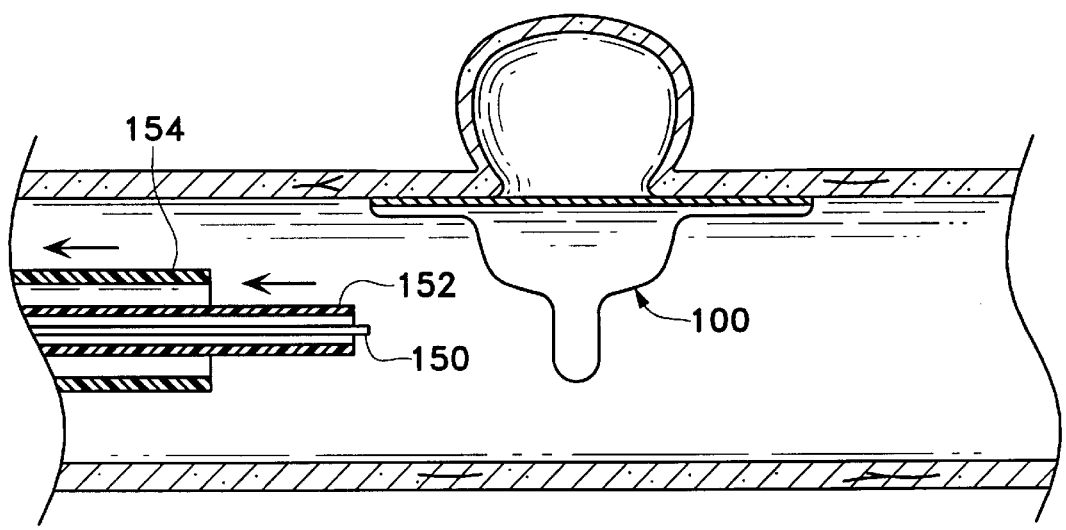

FIG. 7B shows the inventive device (100) in place and the delivery catheter (154) being withdrawn along with sheath (152) and core wire (150).

Figure 8:
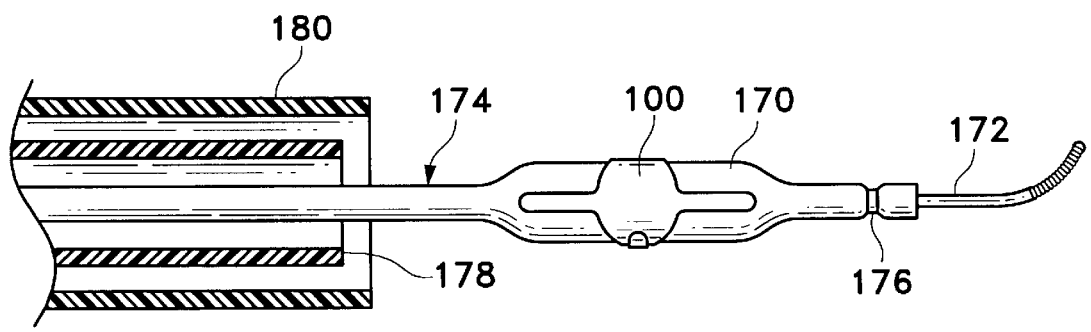
FIG. 8 shows a balloon-based deployment device for deploying the inventive device.

FIG. 8 shows, in partial cross-section, another way of delivering the inventive device to a selected site in the body. In this variation, the neck bridge (100) is likely constructed of a material which is deformable by the use of the balloon (170) into the final shape as outlined in the discussion relating to FIGS. 6A and 6B above. The balloon (170) is not of a critical design except that it be of a size and toughness suitable for expanding the noted device much in the same way that a balloon is used to place a stent. The balloon (170) along with its associated components in the overall assembly may, for instance, be that found in U.S. Pat. No. 5,135,494, to Engelson et al. The guidewire (172) may be used both as a guidewire per se and, in conjunction with a bead placed on the guidewire body, as a valving means for closing the single lumen catheter (174) and inflating the balloon (170). The closing valve seat (176) used in conjunction with the unshown bead on the guidewire body may be seen on the distal portion of the catheter body (174) just proximal of the catheter distal end. An optional sheath (178) is shown the sheath is to protect the neck bridge (100) during its transit through the delivery catheter (180). The device (100) is delivered to the chosen site, the balloon (170) is inflated and the device is left in at the chosen site.

Figure 9:
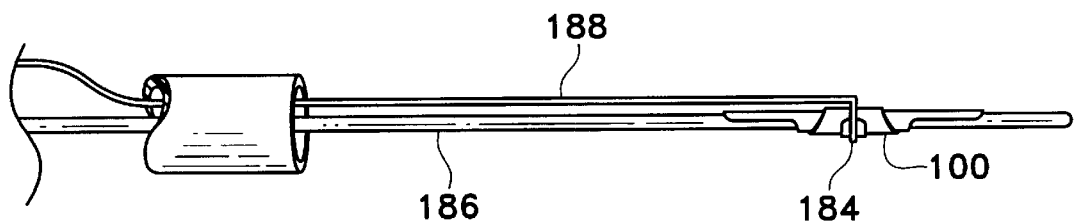
FIG. 9 shows a wire-based deployment device for deploying the inventive device.

FIG. 9 shows another variation in which the inventive device (100) is delivered using an electrolytic joint (184) to secure a self-expanding version of the neck bridge (100). In this variation, a simple wire having the neck bridge (100) wound onto its distal end is introduced into the vasculature. Release of the neck bridge (100) is accomplished by imposition of a current into wire (188). The electrolytic joint (184) erodes and the neck bridge (100) self expands. Use of electrolytic joints in deploying implants is described, for instance, in U.S. Pat. No. 5,122,136, to Guglielmi et al, and others.

The inventive device discussed above may be at least partially covered by, e.g., radio opaque materials to help with the location of the device in the body using a fluoroscope, or with lubricious materials, e.g., fluorocarbonaceous polymers (PTFE, FEP, etc.) or hydrophilics (polyvinylpyrolidone, etc.) or silicones if the user sees such a need.

Many alterations and modifications may be made by those of ordinary skill in this art, without departing from the spirit and scope of this invention. The illustrated embodiments have been shown only for purposes of clarity and the examples should not be taken as limiting the invention as defined in the following claims, which are intended to include all equivalents, whether now or later devised.

We claim as our invention:

1. An aneurysm closure device deliverable through the vasculature comprising a single-piece sheet having a generally central closure region sized to cover at least most of an opening in a selected vascular aneurysm, at least two circumferential struts extending in generally opposite directions from said closure region, and at least two longitudinal struts extending in generally opposite directions from said closure region, generally orthogonal to said circumferential struts, and together of a length sufficient to stabilize said aneurysm closure device from movement when positioned to cover said at least most of an opening in a vascular aneurysm in cooperation with said circumferential struts.

2. The aneurysm closure device of claim 1 wherein said sheet is metallic.

3. The aneurysm closure device of claim 1 wherein said sheet is polymeric.

4. The aneurysm closure device of claim 2 wherein said metallic sheet comprises a superelastic alloy.

5. The aneurysm closure device of claim 4 wherein said superelastic alloy is an Ni/Ti alloy.

6. The aneurysm closure device of claim 2 wherein said metallic sheet comprises a stainless steel alloy.

7. The aneurysm closure device of claim 1 wherein said at least two circumferential struts together are of a length sufficient to overlap some but not all of a circumference of a vascular lumen outside said aneurysm when said aneurysm closure device is positioned to cover said at least most of an opening in a vascular aneurysm.

8. The aneurysm closure device of claim 1 wherein said generally central closure region is sized to cover all of an opening in a selected vascular aneurysm.

9. The aneurysm closure device of claim 1 further comprising one or more vaso-occlusive devices.

10. The aneurysm closure device of claim 1 wherein said sheet comprises a composite of polymers and polymeric fibers.

11. The aneurysm closure device of claim 1 wherein said sheet comprises a composite of polymers and metallic fibers.

* * * * *